US012791555B2

(12) United States Patent
Okawa et al.

(10) Patent No.: US 12,791,555 B2
(45) Date of Patent: Nov. 10, 2026

(54) DETECTION METHOD AND DETECTION DEVICE

(71) Applicant: OTSUKA PHARMACEUTICAL CO., LTD., Tokyo (JP)

(72) Inventors: Eiichi Okawa, Tokyo (JP); Hideyuki Fujii, Tokyo (JP); Kumiko Hoshi, Tokyo (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 1192 days.

(21) Appl. No.: 17/762,481

(22) PCT Filed: Aug. 28, 2020

(86) PCT No.: PCT/JP2020/032548

§ 371 (c)(1),
(2) Date: Mar. 22, 2022

(87) PCT Pub. No.: WO2021/059859

PCT Pub. Date: Apr. 1, 2021

(65) Prior Publication Data

US 2022/0326234 A1 Oct. 13, 2022

(30) Foreign Application Priority Data

Sep. 24, 2019 (JP) ................................ 2019-173299

(51) Int. Cl.
*G01N 33/543* (2006.01)

(52) U.S. Cl.
CPC .............................. *G01N 33/54373* (2013.01)

(58) Field of Classification Search
CPC ........... G01N 33/54373; G01N 21/553; G01N 2021/0382; G01N 2021/0389;
(Continued)

(56) References Cited

U.S. PATENT DOCUMENTS 6,843,963 B1 1/2005 Jennissen et al.
2007/0054415 A1 3/2007 Muraishi
(Continued)

FOREIGN PATENT DOCUMENTS

EP 3495802 A1 6/2019
EP 3584561 A1 12/2019
(Continued)

OTHER PUBLICATIONS

Extended European Search Report dated Jul. 24, 2023 in Application No. 20868145.2.
(Continued)

*Primary Examiner* — Lyle Alexander
*Assistant Examiner* — Dwan A Gerido
(74) *Attorney, Agent, or Firm* — Sughrue Mion, PLLC

(57) ABSTRACT

A detection method uses a reaction vessel including a container including a housing part having a first opening opened at an upper portion and a second opening opened at a side portion, and a side wall member fixed to the container so that a capturing region on a metal film is exposed in the second opening. First, a liquid containing a specimen is provided to the housing part. Next, the liquid in the housing part is stirred to capture, into the capturing region, a substance to be detected in the liquid. Next, the metal film is irradiated with light so that surface plasmon resonance occurs in the metal film, and light emitted from the reaction vessel and having a light amount changing depending on the amount of the substance to be detected captured in the capturing region is detected. In the step of providing the liquid to the housing part, an amount of liquid in which the liquid is not in contact with the capturing region when the liquid in the housing part is left still, and the liquid is in contact with the capturing region when the liquid in the housing part is stirred is provided to the housing part.

4 Claims, 11 Drawing Sheets

(58) Field of Classification Search
CPC .......... G01N 2021/6482; G01N 21/648; B01F 29/20; B01F 29/62; B01F 31/00
See application file for complete search history.

(56) References Cited

U.S. PATENT DOCUMENTS

| | | | |
|---|---|---|---|
| 2009/0296083 A1 | 12/2009 | Saaski et al. | |
| 2018/0001285 A1 * | 1/2018 | Sung | B06B 1/16 |
| 2019/0344261 A1 | 11/2019 | Kaya et al. | |

FOREIGN PATENT DOCUMENTS

| | | | |
|---|---|---|---|
| EP | 3584584 | A1 | 12/2019 |
| JP | 2007-064943 | A | 3/2007 |
| JP | 3935317 | B2 | 6/2007 |
| JP | 2013-148518 | A | 8/2013 |
| JP | 2019-144023 | A | 8/2019 |
| WO | 2008/054282 | A1 | 5/2008 |
| WO | 2016/093037 | A1 | 6/2016 |
| WO | 2018/021238 | A1 | 2/2018 |
| WO | 2018/150943 | A1 | 8/2018 |
| WO | 2018/150944 | A1 | 8/2018 |
| WO | 2019/159626 | A1 | 8/2019 |

OTHER PUBLICATIONS

International Search Report dated Nov. 17, 2020 from the International Searching Authority in International Application No. PCT/JP2020/032548.

International Preliminary Report on Patentability with the translation of Written Opinion dated Mar. 15, 2022 from the International Bureau in International Application No. PCT/JP2020/032548.

* cited by examiner

DETECTION METHOD AND DETECTION DEVICE

CROSS REFERENCE TO RELATED APPLICATIONS

This application is a National Stage of International Application No. PCT/JP2020/032548 filed Aug. 28, 2020, claiming priority based on Japanese Patent Application No. 2019-173299 filed Sep. 24, 2019.

TECHNICAL FIELD

The present disclosure relates to a detection method and a detection device for detecting a substance to be detected.

BACKGROUND ART

In clinical tests and the like, if a trace amount of a substance to be detected (substance to be measured) such as protein of blood or DNA can be detected (measured) with high sensitivity and quantitatively, it is possible to quickly grasp the condition of a patient and perform treatment. For this reason, a method capable of detecting a trace amount of a substance to be detected with high sensitivity and quantitatively is required.

As a method capable of detecting a trace amount of a substance to be detected with high sensitivity, Surface Plasmon Resonance (hereinafter, abbreviated as "SPR") Method and Surface Plasmon-field enhanced Fluorescence Spectroscopy (hereinafter, abbreviated as "SPFS") Method are known. These methods utilize the fact that Surface Plasmon Resonance (SPR) occurs when the metal film is irradiated with light under predetermined conditions. In the SPR method, when the substance to be detected binds to the capturing region on the metal film, the substance to be detected is detected by utilizing the fact that the incident angle at which the amount of reflected light is the smallest changes when light is made incident on the metal film so that SPR occurs. In the SPFS, in a state in which a substance to be detected labeled with a fluorescent substance is bound to a reaction region on a metal film, fluorescence generated from the fluorescent substance when light is made incident on the metal film so that SPR occurs is detected to detect the substance to be detected.

JP 2007-064943 A discloses a method for measuring a substance to be detected (analyte) using the SPR method. The measurement method described in JP 2007-064943 A uses a sensor unit including a prism, a metal film disposed on the prism, a capturing region (linker film) for capturing a substance to be detected disposed on the metal film, and a flow path member fixed to the prism so that the capturing region is exposed in the flow path. A liquid containing a substance to be detected is introduced into the flow path to cause a binding reaction of the substance to be detected to the capturing region, and a cleaning liquid is introduced into the flow path to terminate the binding reaction.

SUMMARY OT THE DISCLOSURE

Problems to be Solved by the Disclosure

However, in the measurement method described in JP 2007-064943 A, in a case where a liquid containing a substance to be detected is retained in the flow path, the concentration of the substance to be detected in the vicinity of the capturing region decreases, and the binding reaction corresponding to the concentration of the substance to be detected in the liquid cannot be performed, and the measurement accuracy decreases. In order not to decrease the measurement accuracy, the liquid containing the substance to be detected may continue to flow in the flow path, but in this case, a large amount of the liquid containing the substance to be detected is required. In addition, in the measurement method described in JP 2007-064943 A, it is difficult to adjust the reaction time of the binding reaction. Therefore, in order to ensure the reproducibility of the measurement result, it is necessary to continuously flow a liquid containing a substance to be detected in the flow path until the binding reaction is saturated.

An object of the present disclosure is to provide a detection method and a detection device capable of detecting a substance to be detected with high accuracy and reproducibility even when the amount of a specimen is small.

Means for Solving the Problems

In order to solve the above problems, a detection method according to an embodiment of the present disclosure is a detection method for detecting a substance to be detected in a specimen using a reaction vessel including: a container including a housing part having a first opening opened at an upper portion and a second opening opened at a side portion; and a side wall member including a prism, a metal film disposed on the prism, and a capturing region for capturing a substance to be detected disposed on the metal film, the side wall member being fixed to the container so that the capturing region is exposed in the second opening, the detection method including the steps of: providing a liquid containing the specimen to the housing part; stirring the liquid in the housing part to capture, into the capturing region, the substance to be detected in the liquid; and irradiating the metal film with light so that surface plasmon resonance occurs in the metal film, and detecting light emitted from the reaction vessel, the light having a light amount changing depending on the amount of the substance to be detected captured in the capturing region, in which in the step of providing the liquid to the housing part, an amount of the liquid, in which the liquid is not in contact with the capturing region when the liquid in the housing part is left still and the liquid is in contact with the capturing region when the liquid in the housing part is stirred, is provided to the housing part.

In order to solve the above problems, a detection device according to an embodiment of the present disclosure is a detection device for detecting a substance to be detected in a specimen using a reaction vessel including: a container including a housing part having a first opening opened at an upper portion and a second opening opened at a side portion; and a side wall member including a prism, a metal film disposed on the prism, and a capturing region for capturing a substance to be detected disposed on the metal film, the side wall member being fixed to the container so that the capturing region is exposed in the second opening, the detection device comprising: a holding part for holding the reaction vessel; a specimen providing unit that provides a liquid containing the specimen to the housing part of the reaction vessel held by the holding part; a light source that irradiates the metal film of the reaction vessel held by the holding part with light so that surface plasmon resonance occurs in the metal film; a detector that detects light emitted from the reaction vessel when the light source irradiates the metal film with light, the light having a light amount changing depending on an amount of a substance to be detected captured in the capturing region; and a stirring part for stirring the liquid in the housing part of the reaction vessel held by the holding part, in which the sample providing unit provides the housing part with an amount of the liquid in which the liquid is not in contact with the capturing region when the liquid in the housing part is left still and the liquid is in contact with the capturing region when the liquid in the housing part is stirred.

According to the present disclosure, it is possible to provide a detection method and a detection device capable of detecting a substance to be detected with high accuracy and reproducibility even when the amount of a specimen is small.

DESCRIPTION OF EMBODIMENTS

Hereinafter, an embodiment of the present disclosure will be described in detail with reference to the drawings.

Embodiment

Figure 1:
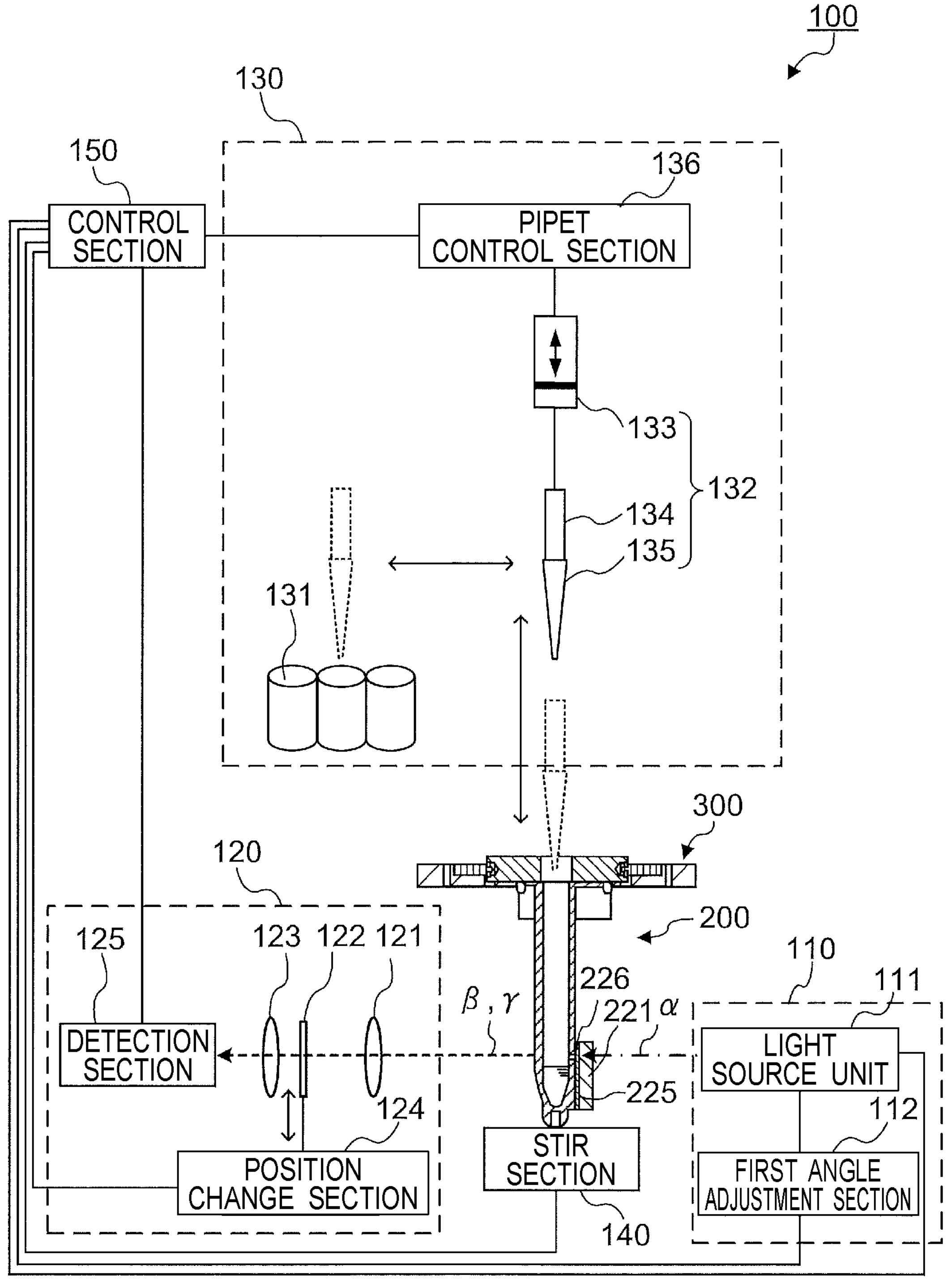
FIG. 1 is a schematic diagram illustrating a configuration of a detection device according to an embodiment of the present disclosure.

FIG. 1 is a schematic diagram illustrating a configuration of a detection device 100 according to an embodiment of the present disclosure. As shown in FIG. 1, the detection device 100 operates in a state where a reaction vessel 200 is attached to a predetermined position (stirring part). In addition to the reaction vessel 200, the detection device 100 includes an excitation light irradiation unit 110, a fluorescence detection unit 120, a liquid feeding unit 130, a stirring part 140, a controller 150, and a holding part 300. In the detection device 100, in a state where the reaction vessel 200 is attached to the holding part 300, the reaction vessel 200 is irradiated with excitation light α so that surface plasmon resonance occurs in a metal film 225 of the reaction vessel 200, and an enhanced electric field based on the surface plasmon resonance is generated in the vicinity of the metal film 225. Then, the fluorescent substance present in a capturing region 226 on the metal film 225 is excited by the enhanced electric field, and fluorescence β emitted by the fluorescent substance is detected, and thereby the presence or absence and an amount of the substance to be detected in the specimen are measured.

Hereinafter, the reaction vessel 200 will be described first, and then the detection device 100 and its operation (detection method) will be described.

(Reaction Vessel)

Figure 2A:
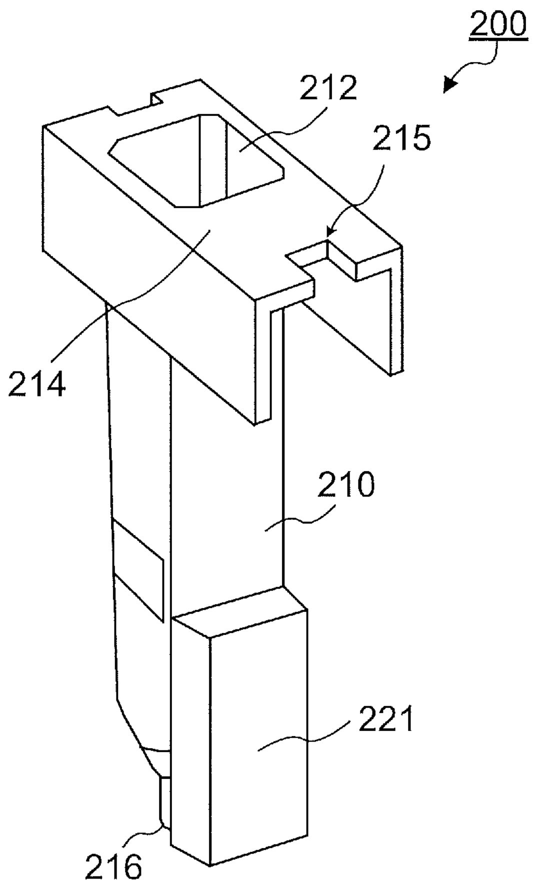
FIG. 2A is a perspective view of a reaction vessel according to an embodiment of the present disclosure.
Figure 2B:
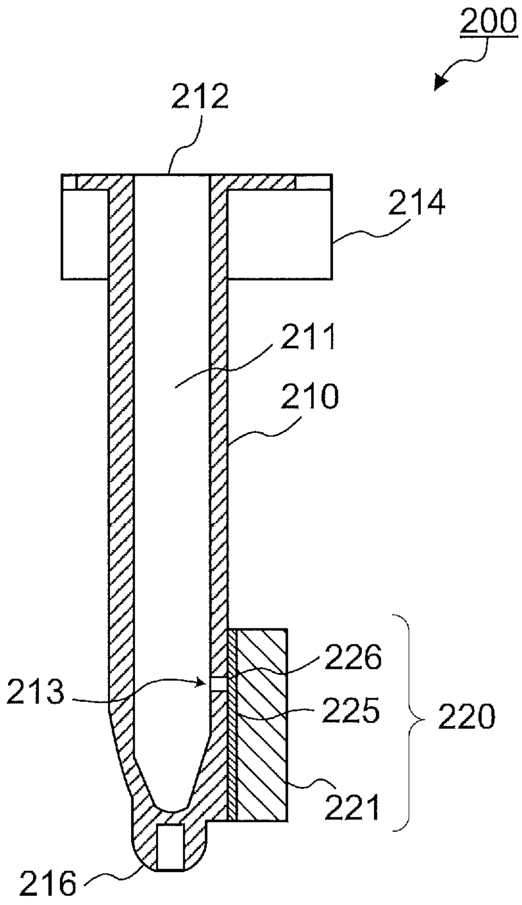
FIG. 2B is a cross-sectional view of the reaction vessel according to an embodiment of the present disclosure.
Figure 2C:
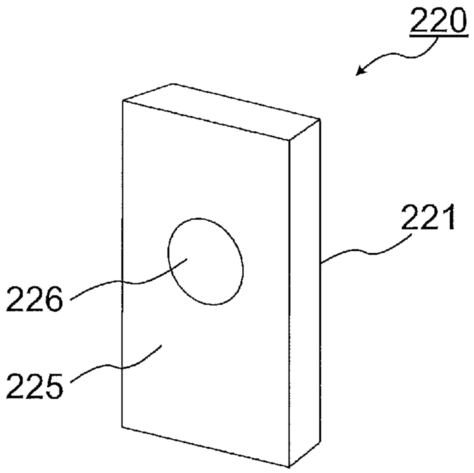
FIG. 2C is a perspective view of a side wall member fixed to the container according to an embodiment of the present disclosure.
Figure 3A:
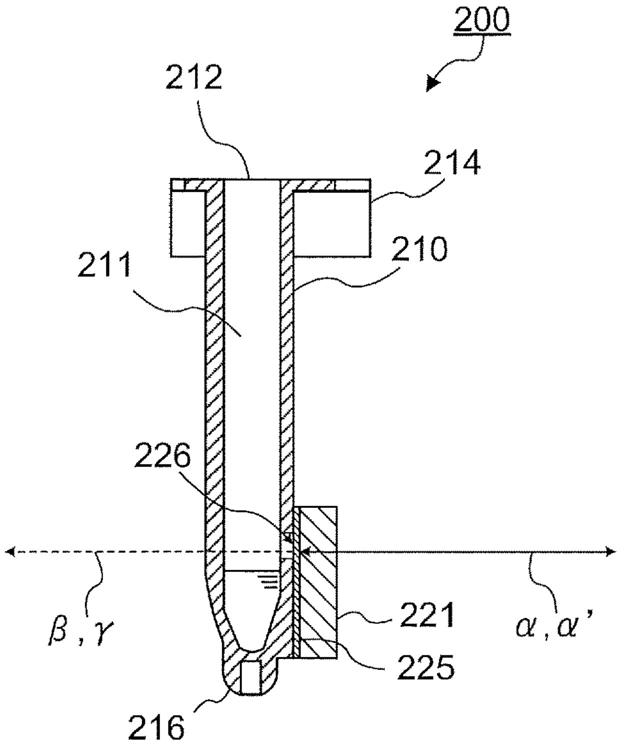
FIGS. 3A and 3B are schematic views illustrating light incident on a reaction vessel and light emitted from the reaction vessel according to an embodiment of the present disclosure.
Figure 3B:
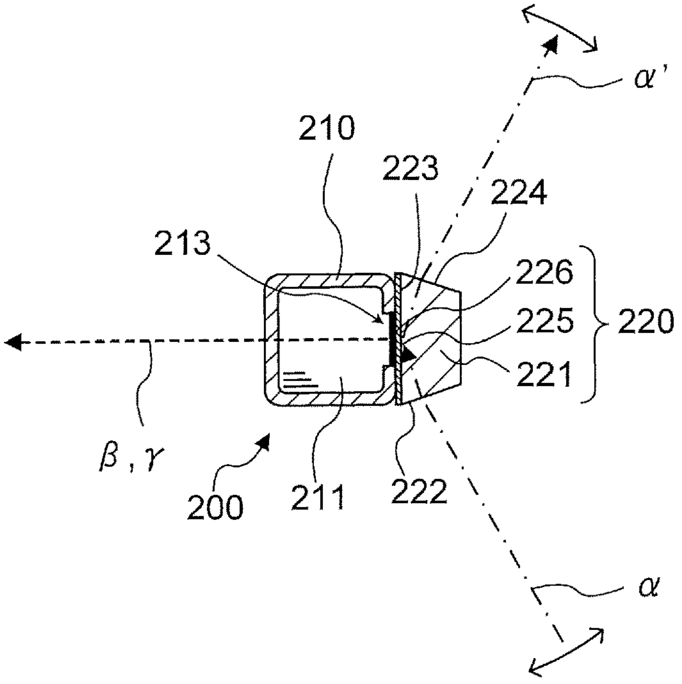
Figure 4:
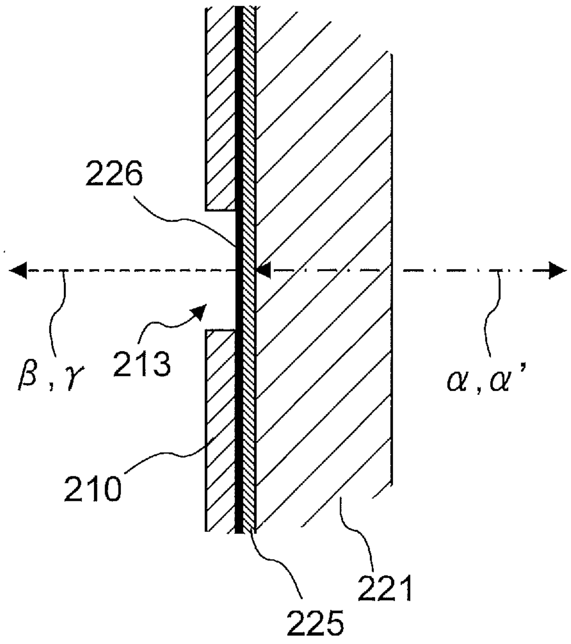
FIG. 4 is a partially enlarged cross-sectional view in which a capturing region in the cross-sectional view of FIG. 3A is enlarged.

FIGS. 2A to 2C are schematic views showing a configuration of the reaction vessel 200 according to an embodiment of the present disclosure. FIG. 2A is a perspective view of the reaction vessel 200, FIG. 2B is a cross-sectional view of the reaction vessel 200, and FIG. 2C is a perspective view of a side wall member 220 fixed to a container 210. FIGS. 3A and 3B are schematic diagrams illustrating light (excitation light α) incident on the reaction vessel 200 and light (fluorescence β and plasmon scattered light γ) emitted from the reaction vessel 200. FIG. 3A is a cross-sectional view taken along the height direction of the reaction vessel 200, and FIG. 3B is a horizontal cross-sectional view of FIG. 3A. FIGS. 3A and 3B illustrate a state in which a liquid (for example, a measurement buffer solution) is housed in a housing part 211. FIG. 4 is a partially enlarged cross-sectional view in which the vicinity of the capturing region 226 in the cross-sectional view of FIG. 3A is enlarged.

As shown in FIGS. 2A and 2B, the reaction vessel 200 has the container 210 and the side wall member 220.

The container 210 has a housing part 211 therein. The housing part 211 is a bottomed recess configured to house liquid, and is opened to the outside by a first opening 212 provided in an upper portion and a second opening 213 provided in a side portion. The first opening 212 is used to provide liquid in the housing part 211 or to remove liquid in the housing part 211. The second opening 213 is formed to expose a capturing region 226 of the side wall member 220 described later in the housing part 211 (see FIG. 4). The second opening 213 is closed by the side wall member 220 so that liquid can be housed in the housing part 211. In the present embodiment, as illustrated in FIGS. 2B and 3B, the second opening 213 is a through hole formed in a side wall on the side wall member 220 side among four side walls constituting the housing part 211.

In addition, the container 210 has a held portion 214 protruding laterally from an upper portion thereof. The held portion 214 has a recess 215 formed by cutting out a part thereof in a substantially rectangular shape. The recess 215 is formed to fix the held portion 214 and an external holding part 300 (described later). The step (described later) of stirring the liquid in the housing part 211 is performed in a state where the held portion 214 of the reaction vessel 200 is held by the holding part 300.

As shown in FIGS. 2B and 3A, a portion (a bottom portion 216 of the container 210) in contact with the stirring part 140 (described later) of the container 210 is preferably a protrusion in a substantially spherical-segment shape (for example, in a substantially hemispherical shape) or a substantially conical recess. The shape of the bottom portion 216 of the container 210 can be appropriately selected according to the shape of the stirring part 140. For example, when the shape of the stirring part 140 is a protrusion having a protrusion in a substantially spherical-segment shape (for example, in a substantially hemispherical shape), the shape of the bottom portion 216 is preferably a substantially conical recess, and when the shape of the stirring part 140 is a substantially conical shape, the shape of the bottom portion 216 is preferably a substantially spherical recess. By combining the stirring part 140 and the bottom portion 216 in contact with each other, it is possible to perform stirring such that the liquid swirls in the housing part 211, so that the liquid efficiently comes into contact with the capturing region 226 and the substance to be detected is easily captured.

Note that the bottom portion of the housing part 211 preferably has a recessed shape (for example, a round bottom) with a recessed center. By forming the shape of the bottom portion of the housing part 211 into a recessed shape (for example, a round bottom) in which the center is recessed, it is possible to more reliably remove the liquid in the housing part 211 and to improve the detection accuracy.

In the reaction vessel 200 according to the present embodiment, light (fluorescence β or plasmon scattered light γ) emitted from the vicinity of the capturing region 226 passes through a side wall facing the capturing region 226 and is detected by a detector 125 (described later) (see FIG. 3B). Therefore, when it is desired to suppress refraction of the light to be detected, as illustrated in FIG. 3B, it is preferable that both the inner surface and the outer surface of the side wall facing the capturing region 226 in the housing part 211 are flat surfaces. Note that the shape of the container 210 is not particularly limited as long as the container has the housing part 211, the first opening 212, and the second opening 213.

The container 210 is formed of a material transparent to light (at least light having a wavelength of excitation light a and light having a wavelength of fluorescence β). However, a part of the container 210 may be formed of a material opaque to light as long as it does not hinder light extraction in a detection method described later. At least the side wall facing the capturing region 226 among the four side walls constituting the housing part 211 has light permeability. Examples of materials that are transparent to light include resins and glass.

The side wall member 220 includes a prism 221 as an optical element, a metal film 225, and a capturing region 226 (see FIG. 2C). Here, the "capturing region" is a region disposed on the metal film 225, and means a region in the housing part 211 through the second opening 213 (see FIG. 4). As shown in FIGS. 2B, 3A, 3B, and 4, the side wall member 220 is fixed to the container 210 so that the capturing region 226 is exposed in the housing part 211 and so that the side wall member 220 completely closes at least a part of the second opening 213. In the present embodiment, the side wall member 220 is bonded to the container 210 via an adhesive layer (not shown) such as a double-sided tape so as to close the entire second opening 213. The side wall member 220 may be joined to the container 210 by laser welding, ultrasonic welding, pressure bonding using a clamp member, or the like without using an adhesive layer.

The prism 221 is an optical element made of a dielectric material transparent to excitation light α, and has an incident surface 222, a reflecting surface 223, and an outgoing surface 224 as illustrated in FIG. 3B. The prism 221 functions also as a side wall constituting the housing part 211. The incident surface 222 is a surface for allowing the excitation light α from the excitation light irradiation unit 110 to be incident on the inside of the prism 221. The excitation light α incident on the inside of the prism 221 is reflected by the reflecting surface 223. As will be described later, the metal film 225 and the capturing region 226 are sequentially arranged on the reflecting surface 223. The outgoing surface 224 is a surface for outputting the reflected light α' reflected by the reflecting surface 223 to the outside of the prism 221.

The shape of the prism 221 is not particularly limited, but the reflecting surface 223 is preferably a flat surface. Examples of the shape of the prism 221 include a columnar body having a trapezoidal bottom surface, a triangular prism, and a semicircular prism. In the present embodiment, the prism 221 has a columnar shape having a trapezoidal bottom surface. A surface corresponding to the lower base of the trapezoid is the reflecting surface 223, a surface corresponding to one leg is the incident surface 222, and a surface corresponding to the other leg is the outgoing surface 224.

The incident surface 222 is preferably formed so that the excitation light α does not return to the excitation light irradiation unit 110. In a case where the light source of the excitation light α is a laser diode (hereinafter, also referred to as "LD"), when the excitation light α returns to the LD, the excited state of the LD is disturbed, and the wavelength and output of the excitation light α fluctuate. Therefore, it is preferable to set the angle of the incident surface 222 so that the excitation light α is not perpendicularly incident on the incident surface 222 in a scanning range centered on an ideal resonance angle or enhancement angle. Here, the "resonance angle" means an incident angle when the light amount of the reflected light α' output from the outgoing surface 224 is minimized in a case where the incident angle of the excitation light α with respect to the reflecting surface 223 (metal film 225) is scanned. Furthermore, the "enhancement angle" means an incident angle when the light amount of scattered light (plasmon scattered light) γ having the same wavelength as the excitation light α emitted from the periphery of the capturing region 226 into the housing part 211 is maximized in a case where the incident angle of the excitation light α with respect to the reflecting surface 223 (metal film 225) is scanned. In the present embodiment, both the angle between the incident surface 222 and the reflecting surface 223 and the angle between the reflecting surface 223 and the outgoing surface 224 are about 80°.

Note that, the resonance angle and the enhancement angle in the very vicinity thereof are roughly determined by the design of the reaction vessel 200. The design elements are the refractive index of the prism 221, the refractive index of the metal film 225, the film thickness of the metal film 225, the extinction coefficient of the metal film 225, the wavelength of the excitation light α, and the like. The resonance angle and the enhancement angle are shifted by the substance to be detected captured in the capturing region 226 on the metal film 225, but the amount thereof is less than several degrees.

The prism 221 has not a little birefringence characteristics. Examples of the material of the prism 221 include resin and glass. The material of the prism 221 is preferably a resin having a refractive index of 1.4 to 1.6 and small birefringence.

The metal film 225 is disposed on the reflecting surface 223 of the prism 221. As a result, an interaction (SPR) occurs between photons of the excitation light α incident on the reflecting surface 223 under the total reflection condition and free electrons in the metal film 225, and an enhanced electric field localized on the surface of the metal film 225 is generated.

The material of the metal film 225 is not particularly limited as long as it is a metal capable of causing surface plasmon resonance. Examples of the material of the metal film 225 include gold, silver, copper, aluminum, and alloys thereof. A method for forming the metal film 225 is not particularly limited. Examples of the method for forming the metal film 225 include sputtering, vapor deposition, and plating. The thickness of the metal film 225 is not particularly limited, but is preferably in the range of 30 to 70 nm.

The capturing region 226 is a region exposed in the housing part 211 for capturing the substance to be detected. As described above, the capturing region 226 means a region disposed on the metal film 225 and exposed in the housing part 211 through the second opening 213. As shown in FIG. 4, when the size of the capturing region 226 is a size capable of closing the second opening 213, the range of the capturing region 226 is defined by the second opening 213. With such a configuration, the size of the capturing region 226 can be easily adjusted with high accuracy.

The capturing region 226 is disposed on the internal surface of the housing part 211. At this time, the capturing region 226 is preferably disposed at a position away from the deepest portion of the housing part 211. With such a configuration, when liquid containing a specimen is introduced into the housing part 211, it is possible to prevent contact between the capturing region 226 and the liquid in a stationary state. In addition, at the time of detecting the fluorescence β, it is also possible to suppress noise caused by the bottom portion of the housing part 211 from being mixed in the detection result.

As described above, the capturing region 226 is a region for capturing the substance to be detected on the metal film 225, and is a region on which a first capturing body is immobilized. The first capturing body is a substance having a recognition site for specifically binding to the substance to be detected in the specimen. When the first capturing body is fixed to the capturing region 226, a liquid containing a specimen is introduced into the housing part 211, and the capturing region 226 and the liquid come into contact with each other, the substance to be detected selectively binds to the first capturing body. That is, the substance to be detected is captured in the capturing region 226. This makes it possible to detect the substance to be detected as described later. The type of the first capturing body is not particularly limited as long as it has a recognition site for specifically binding to the substance to be detected. Examples of the first capturing body include an antibody (primary antibody) or a fragment thereof capable of specifically binding to the substance to be detected, an enzyme capable of specifically binding to the substance to be detected, and the like.

From the viewpoint of improving the detection accuracy, the surface on which the capturing region 226 is disposed is preferably a flat surface. That is, when the capturing region 226 is disposed on the metal film 225 as in the present embodiment, the surface of the metal film 225 is preferably a flat surface.

(Holding Part)

Figure 5A:
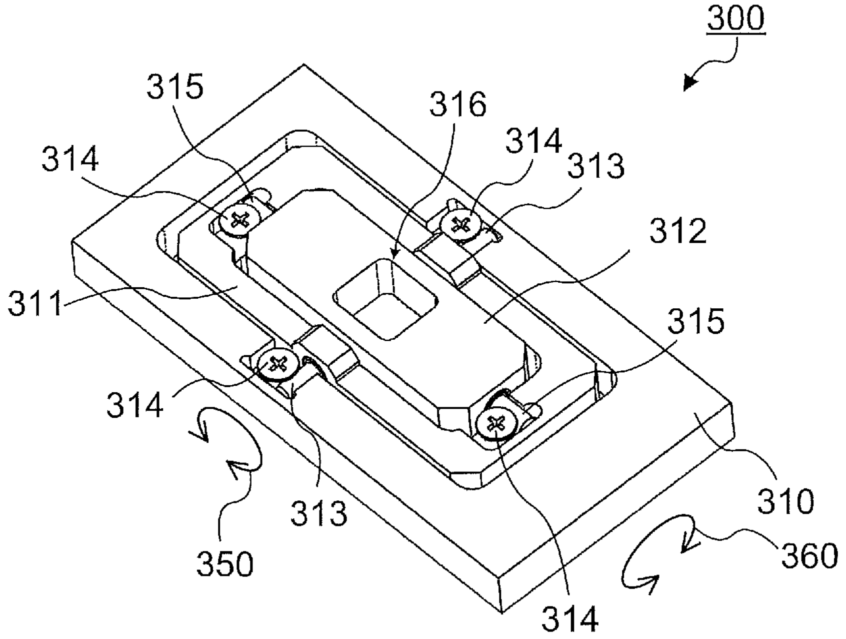
FIG. 5A is a perspective view of a holding part for holding a holding part of the reaction vessel according to an embodiment of the present disclosure.
Figure 5B:
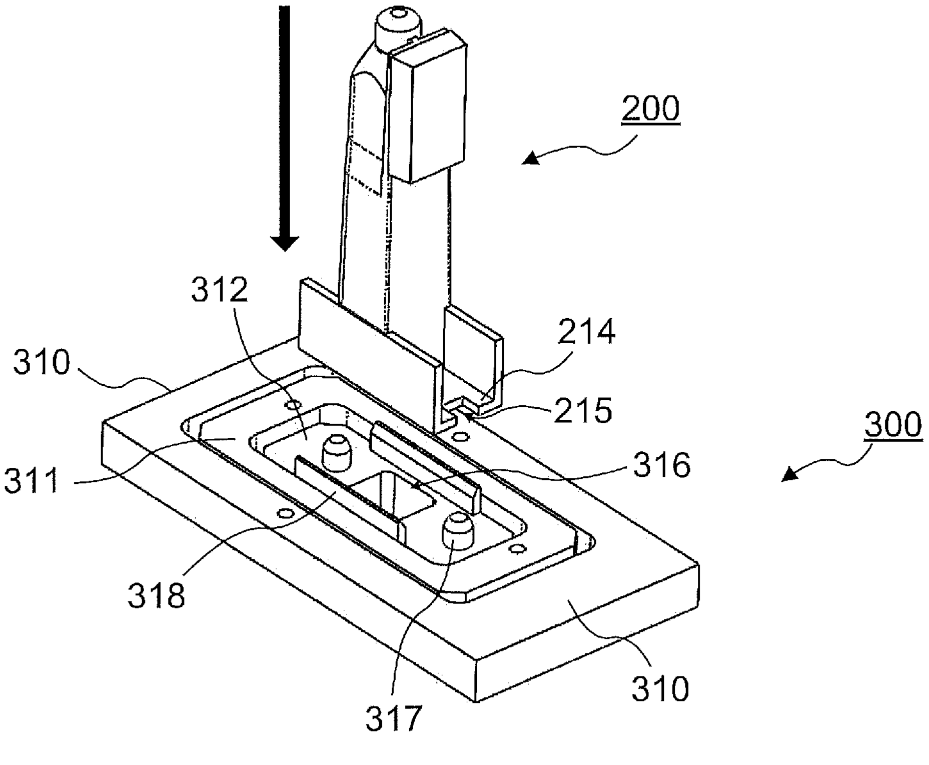
FIG. 5B is a perspective view illustrating a state in which the reaction vessel is attached to the holding part.
Figure 6A:
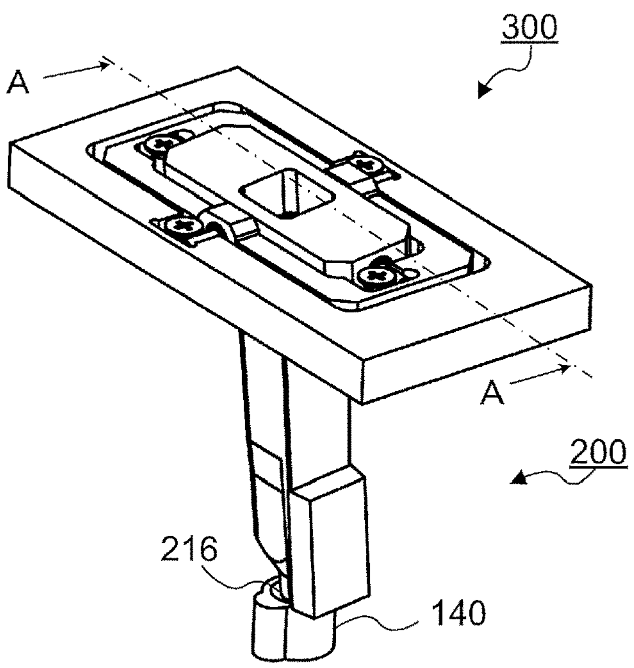
FIG. 6A is a perspective view illustrating a state in which a bottom portion of the reaction vessel to which the holding part is attached is brought into contact with the stirring part.
Figure 6B:
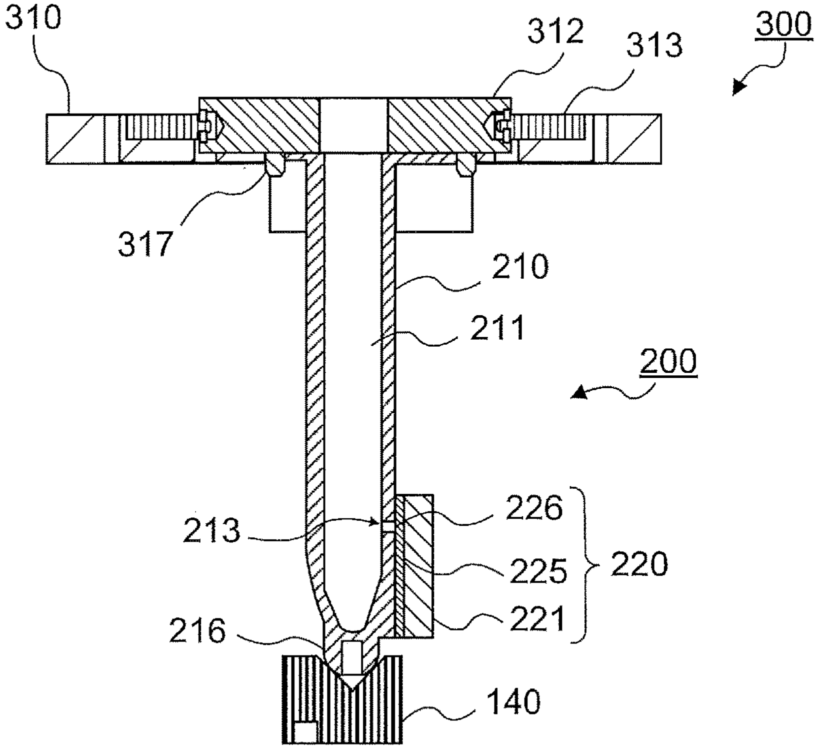
FIG. 6B is a cross-sectional view illustrating a state in which the bottom portion of the reaction vessel to which the holding part is attached is brought into contact with the stirring part.
Figure 7A:
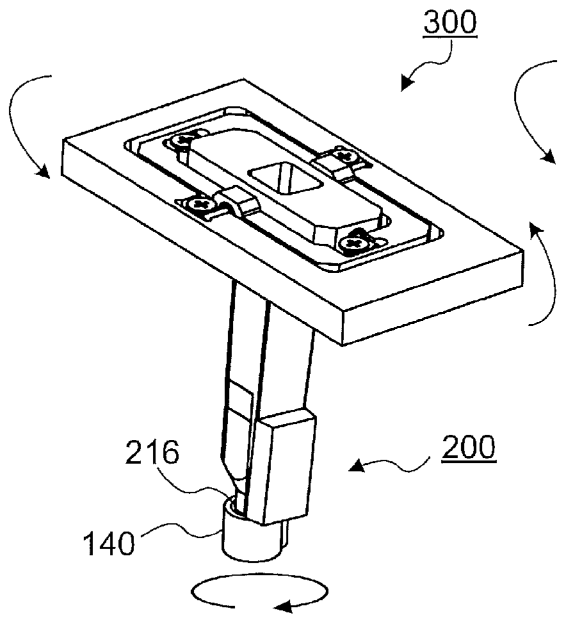
FIGS. 7A to 7D are perspective views showing a stirring operation of the reaction vessel according to an embodiment of the present disclosure.
Figure 7B:
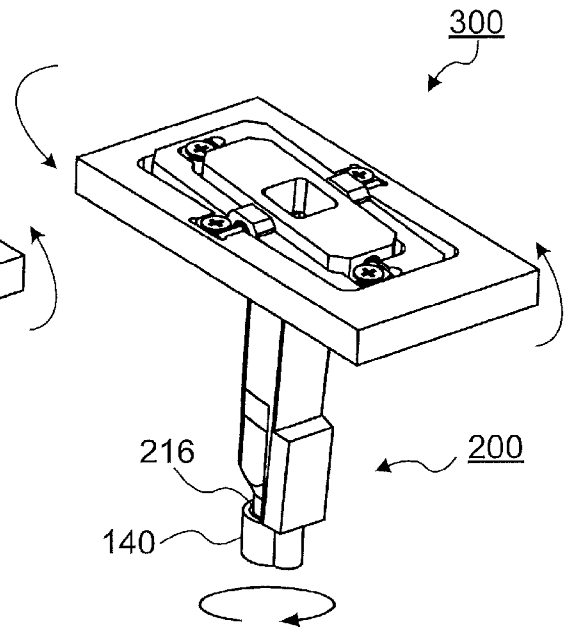
Figure 7C:
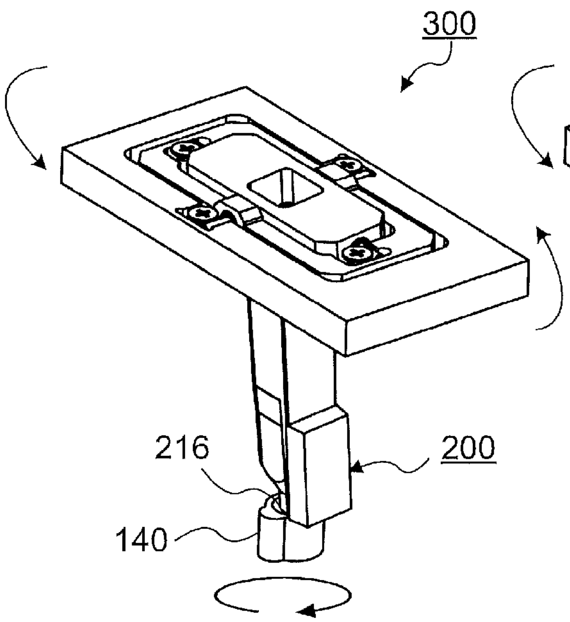
Figure 7D:
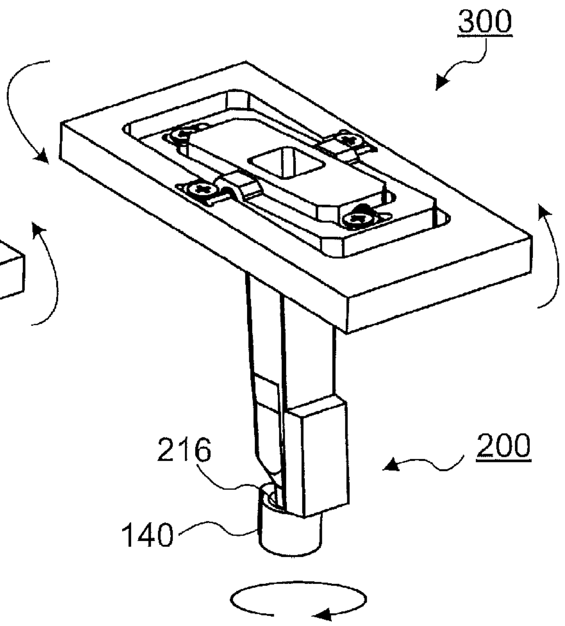

FIG. 5A is a perspective view of the holding part 300 for holding the held portion 214 of the reaction vessel 200 according to an embodiment of the present disclosure, and FIG. 5B is a perspective view illustrating a state in which the held portion 214 of the reaction vessel 200 is attached to the holding part 300 of the detection device 100. FIG. 6A is a perspective view showing a state in which the reaction vessel 200 is fixed to the holding part 300 and placed on the stirring part 140 of the detection device 100, and FIG. 6B is a cross-sectional view taken along a line A-A of FIG. 6A. FIGS. 7A to 7D are perspective views showing the movement of the holding part 300 when the reaction vessel 200 is stirred by the stirring part 140.

As illustrated in FIG. 5A, the holding part 300 includes a first substrate 310, a second substrate 311 disposed inside the first substrate 310, and a third substrate 312 disposed inside the second substrate 311. A first rotary shaft 313 extending in a first direction is provided between the first substrate 310 and the second substrate 311 so that the second substrate 311 is rotatable in a first rotation direction 350 with respect to the first substrate 310. The first rotary shaft 313 is fixed to the first substrate 310 by fixing members 314, and the second substrate 311 is rotatably held by the first rotary shaft 313. Similarly, a second rotary shaft 315 extending in a second direction orthogonal to the first direction is provided between the second substrate 311 and the third substrate 312 so that the third substrate 312 is rotatable in a second rotation direction 360 with respect to the second substrate 311. The second rotary shaft 315 is also fixed to the second substrate 311 by fixing members 314, and the third substrate 312 is rotatably held by the second rotary shaft 315. The first rotary shaft 313 is provided so that the holding part 300 rotatably holds the held portion 214 in the first rotation direction 350, and the second rotary shaft 315 is provided so that the holding part 300 rotatably holds the held portion 214 in the second rotation direction 360. In addition, a third opening 316 having substantially the same shape as the first opening 212 of the reaction vessel 200 is formed in the central portion of the third substrate 312. In the present embodiment, the size of the third opening 316 is slightly larger than that of the first opening 212 of the reaction vessel 200 (see FIG. 6B).

As shown in FIG. 5B, a plurality of protrusions 317 for fixing the held portion 214 of the reaction vessel 200 and fixing plates 318 for holding a side surface of the held portion 214 are formed on the back surface side of the third substrate 312. The held portion 214 of the reaction vessel 200 is inserted between the fixing plates 318 in the direction of the arrow so that the first opening 212 of the reaction vessel 200 coincides with the third opening 316 of the holding part 300, whereby the reaction vessel is attached to the holding part 300. As shown in FIGS. 6A and 6B, the reaction vessel 200 attached to the holding part 300 is placed on the stirring part 140. As shown in FIGS. 7A to 7D, by operating (turning) the stirring part 140, the bottom portion 216 of the reaction vessel 200 in contact with the stirring part 140 turns, the liquid provided to the housing part 211 is stirred so as to draw a vortex, and the liquid and the capturing region 226 come into contact with each other (see FIG. 9A). Note that the material of the holding part 300 is not particularly limited as long as the holding part 300 has strength enough to withstand stirring in a state in which the reaction vessel 200 is attached. Further, the method for fixing the reaction vessel is not particularly limited as long as the reaction vessel 200 and the holding part 300 are not detached from each other during stirring of the reaction vessel 220.

(Detection Device)

Next, components of the detection device 100 will be described. As described above, the detection device 100 includes the excitation light irradiation unit 110, the fluorescence detection unit 120, the liquid feeding unit 130, the stirring part 140, the controller 150, and the holding part 300 in addition to the reaction vessel 200 (see FIG. 1).

The excitation light irradiation unit 110 irradiates the reaction vessel 200 with the excitation light α. At the time of measuring the fluorescence β or the plasmon scattered light γ, the excitation light irradiation unit 110 emits only the P waves with respect to the reflecting surface 223 (metal film 225) toward the incident surface 222 of the prism 221 so that the incident angle with respect to the reflecting surface 223 (metal film 225) of the prism 221 becomes an angle at which SPR occurs in the metal film 225. Here, the "excitation light" is light that directly or indirectly excites a fluorescent substance. For example, the excitation light α is light that generates an enhanced electric field for exciting the fluorescent substance on the surface of the metal film 225 when the reflecting surface 223 (metal film 225) is irradiated with the excitation light α through the prism 221 at an angle at which SPR occurs in the metal film 225. The excitation light irradiation unit 110 includes a light source unit 111 and a first angle adjuster 112.

The light source unit 111 emits the collimated excitation light α having a constant wavelength and light amount so that the shape of the irradiation spot on the reflecting surface 223 (the surface of the metal film 225) is substantially circular. The size of the irradiation spot is preferably smaller than that of the capturing region 226 of the reaction vessel 200. The light source unit 111 includes, for example, a light source of the excitation light α, a beam shaping optical system, an APC mechanism, and a temperature adjustment mechanism (all not illustrated). Note that the shape of the irradiation spot is preferably substantially circular, but may not be substantially circular.

The type of the light source is not particularly limited, and is, for example, a laser diode (LD). Other examples of light sources include light emitting diodes, mercury lamps, and other laser light sources. When the light emitted from the light source is not a beam, the light emitted from the light source is converted into a beam by a lens, a mirror, a slit, or the like. In addition, in a case where the light emitted from the light source is not monochromatic light, the light emitted from the light source is converted into monochromatic light by a diffraction grating or the like. Further, in a case where the light emitted from the light source is not linearly polarized light, the light emitted from the light source is converted into linearly polarized light by a polarizer or the like.

The beam shaping optical system includes, for example, a collimator, a bandpass filter, a linear polarization filter, a half-wave plate, a slit, a zoom means, and the like. The beam shaping optical system may include all or a part thereof. The collimator collimates the excitation light α emitted from the light source. The bandpass filter makes the excitation light α emitted from the light source narrowband light having only the center wavelength. This is because the excitation light α from the light source has a slight wavelength distribution width. The linear polarization filter converts the excitation light α emitted from the light source into completely linearly polarized light. The half-wave plate adjusts the polarization direction of the excitation light α so that the P wave component is incident on the reflecting surface 223. The slit and the zoom means adjust the beam diameter, the contour shape, and the like of the excitation light α so that the shape of the irradiation spot on the reflecting surface 223 becomes a circle of a predetermined size.

The APC mechanism controls the light source so that the output of the light source is constant. More specifically, the APC mechanism detects the amount of light branched from the excitation light α with a photodiode (not illustrated) or the like. Then, the APC mechanism controls the output of the light source to be constant by controlling the input energy by the regression circuit.

The temperature adjustment mechanism is, for example, a heater or a Peltier element. The wavelength and energy of the light emitted from the light source may vary with temperature. Therefore, by keeping the temperature of the light source constant by the temperature adjustment mechanism, the wavelength and energy of the light emitted from the light source are controlled to be constant.

The first angle adjuster 112 adjusts the incident angle of the excitation light α with respect to the reflecting surface 223. The first angle adjuster 112 relatively rotates the optical axis of the excitation light a and the reaction vessel 200 in order to emit the excitation light α at a predetermined incident angle toward a predetermined position of the reflecting surface 223 through the prism 221.

For example, the first angle adjuster 112 rotates the light source unit 111 about an axis orthogonal to the optical axis of the excitation light α (an axis along the height direction of the reaction vessel 200) (see FIG. 3B). At this time, the position of the rotary shaft is set so that the position of the irradiation spot on the reflecting surface 223 hardly changes even if the incident angle is scanned.

As described above, the angle at which the light amount of the plasmon scattered light γ is maximized among the incident angles of the excitation light α with respect to the reflecting surface 223 (metal film 225) is the enhancement angle. By setting the incident angle of the excitation light α to an enhancement angle or an angle in the vicinity thereof (for example, a resonance angle), it is possible to measure the fluorescence β with high intensity. Although the basic incident condition of the excitation light α is determined by the material and shape of the prism 221 of the reaction vessel 200, the film thickness of the metal film 225, the refractive index of the liquid in the housing part 211, and the like, the optimum incident condition slightly varies depending on the type and amount of the fluorescent substance to be used, the shape error of the prism 221, and the like. Therefore, it is preferable to obtain an optimum enhancement angle for each detection.

The fluorescence detection unit 120 detects fluorescence β emitted when the light source unit 111 irradiates the reflecting surface 223 (metal film 225) with the excitation light α. In the present embodiment, the fluorescence β corresponds to light whose light amount changes depending on the amount of the substance to be detected captured by the capturing region 226. In addition, if necessary, the fluorescence detection unit 120 also detects the plasmon scattered light γ generated when the light source unit 111 irradiates the reflecting surface 223 (metal film 225) with the excitation light α. The fluorescence detection unit 120 includes a first lens 121, an optical filter 122, a second lens 123, a position switching unit 124, and a detector 125.

The first lens 121 is, for example, a condenser lens, and condenses light emitted from the vicinity of the capturing region 226. The second lens 123 is, for example, an image forming lens, and forms an image of the light condensed by the first lens 121 on the light receiving surface of the detector 125. The optical paths between the two lenses are substantially parallel optical paths. The optical filter 122 is disposed between both lenses.

The optical filter 122 guides only the fluorescence component to the detector 125 and removes the excitation light component (plasmon scattered light γ) in order to detect the fluorescence β at a high signal (S)/noise (N) ratio. Examples of the optical filter 122 include an excitation light reflection filter, a short wavelength cut filter, and a bandpass filter. The optical filter 122 is, for example, a filter including a multilayer film that reflects a predetermined light component or a color glass filter that absorbs a predetermined light component.

The position switching unit 124 switches the position of the optical filter 122 onto the optical path or the outside of the optical path between the first lens 121 and the second lens 123. Specifically, the optical filter 122 is disposed on the optical path when the detector 125 detects the fluorescence β, and the optical filter 122 is disposed outside the optical path when the detector 125 detects the plasmon scattered light γ.

The detector 125 is a light receiving sensor that detects the fluorescence β and the plasmon scattered light γ. The detector 125 has high sensitivity capable of detecting weak fluorescence β from a minute amount of the substance to be detected. The detector 125 is, for example, a photomultiplier tube (PMT), an avalanche photodiode (APD), or the like.

As shown in FIGS. 1 and 3A, in the present embodiment, the excitation light α from the light source unit 111 travels in the horizontal direction and reaches the reaction vessel 200. Furthermore, light (fluorescence β or plasmon scattered light γ) emitted from the vicinity of the capturing region 226 and traveling in the horizontal direction is detected by the detector 125. Therefore, in the present embodiment, the light source unit 111 and the detector 125 are arranged at the same height as the reaction vessel 200. Of course, the positions of the light source unit 111 and the detector 125 can be freely changed by using a mirror or the like, but from the viewpoint of miniaturization, the light source unit 111 and the detector 125 are preferably arranged at the same height as the reaction vessel 200.

The liquid feeding unit 130 provides various liquids in the housing part 211 of the reaction vessel 200. In addition, the liquid feeding unit 130 removes various liquids from the inside of the housing part 211 of the reaction vessel 200. In the present embodiment, the liquid feeding unit 130 performs injection and suction of, for example, a liquid containing a specimen, a labeling liquid containing a second capturing body labeled with a fluorescent substance (hereinafter also referred to as "labeling liquid"), a cleaning liquid, a measurement buffer solution, and the like. The liquid feeding unit 130 functions as a specimen providing unit that provides a liquid containing a specimen to the housing part 211 of the reaction vessel 200 held by the holding part 300. The liquid feeding unit 130 includes liquid tips 131, a pipette 132, and a pipette controller 136.

The liquid tips 131 are containers for housing liquids such as a specimen and a labeling liquid, a cleaning liquid, and a measurement buffer solution, respectively. As the liquid tip 131, usually, a plurality of containers are arranged depending on the type of liquids, or a tip in which a plurality of containers are integrated is disposed.

The pipette 132 includes a syringe pump 133, a nozzle unit 134 connected to the syringe pump 133, and a pipette tip 135 attached to the tip of the nozzle unit 134. The reciprocating motion of the plunger in the syringe pump 133 quantitatively causes suction and discharge of liquid in the pipette tip 135.

The pipette controller 136 includes a driving device of the syringe pump 133 and a moving device of the nozzle unit 134. The driving device of the syringe pump 133 is a device for reciprocating the plunger of the syringe pump 133, and includes, for example, a stepping motor. For example, the moving device of the nozzle unit 134 freely moves the nozzle unit 134 in two directions of the vertical direction and the horizontal direction. The moving device of the nozzle unit 134 includes, for example, a robot arm, a biaxial stage, or a vertically movable turntable.

The pipette controller 136 drives the syringe pump 133 to suck various liquids from the liquid tip 131 into the pipette tip 135. Then, the pipette controller 136 moves the nozzle unit 134 to insert the pipette tip 135 into the housing part 211 of the reaction vessel 200 from the first opening 212, and drives the syringe pump 133 to inject the liquid in the pipette tip 135 into the housing part 211. In addition, after the introduction of the liquid, the pipette controller 136 drives the syringe pump 133 to suck the liquid in the housing part 211 into the pipette tip 135. By sequentially exchanging the liquid in the housing part 211 in this manner, the first capturing body and the substance to be detected are reacted in the capturing region 226 (primary reaction), or the substance to be detected and the second capturing body labeled with the fluorescent substance are reacted (secondary reaction). Note that, as described later, when a liquid containing a specimen is provided to the housing part 211 of the reaction vessel 200 held by the holding part 300, the pipette controller 136 controls, under the control of the controller 150, the amount of liquid to be provided in the housing part 211 so that the liquid does not come into contact with the capturing region 226 when the liquid in the housing part 211 is left still and the liquid comes into contact with the capturing region 226 when the liquid in the housing part 211 is stirred.

The stirring part 140 turns the reaction vessel 200 in order to stir the liquid in the housing part 211 of the reaction vessel 200 held by the holding part 300. As described above, the portion where the stirring part 140 is in contact with the container 210 (the bottom portion 216 of the container 210) is preferably a protrusion in a substantially spherical-segment shape or a substantially conical recess. The shape of the stirring part 140 can be appropriately selected according to the shape of the bottom portion 216 of the container 210. For example, when the shape of the stirring part 140 is a protrusion in a substantially spherical-segment shape, the shape of the bottom portion 216 is preferably a substantially conical recess, and when the shape of the stirring part 140 is a substantially conical shape, the shape of the bottom portion 216 is preferably a substantially spherical recess. By combining the stirring part 140 and the bottom portion 216 in contact with each other, it is possible to perform stirring such that the liquid swirls in the housing part 211, so that the liquid efficiently comes into contact with the capturing region 226 and the substance to be detected is easily captured. By operating the stirring part 140 to turn the reaction vessel 200 and stir the liquid provided in the housing part 211 in a swirling manner, the primary reaction, the secondary reaction, the cleaning, and the like in the capturing region 226 can be efficiently performed. The stirring part 140 is, for example, a piezoelectric element or an eccentric rotating body. The stirring part 140 is disposed at a position not interfering with the optical paths of the excitation light α, the fluorescence β, and the plasmon scattered light γ.

The rotation speed at which the reaction vessel 200 is turned is preferably 1500 to 3000 rpm. By setting the rotation speed to 1500 to 3000 rpm, even if the amount of liquid provided in the housing part 211 is an amount that is not in contact with the capturing region 226 when the liquid is left still, the liquid can be easily brought into contact with the capturing region when the liquid is stirred. From the viewpoint of efficiently bringing the liquid in the housing part 211 into contact with the capturing region 226, the amount of liquid provided in the housing part 211 is preferably an amount that comes to a position 1 to 3 mm below the height at which the capturing region 226 is disposed.

In addition, by rotating the rotating body in a state in which an eccentric rotating body (not illustrated) as the stirring part 140 is in contact with the bottom portion 216 of the reaction vessel 200, rotational vibration in the circumferential direction may be applied to the reaction vessel 200 to stir the liquid in the housing part 211 and bring the liquid into contact with the capturing region 226.

The controller 150 controls the light source unit 111, the first angle adjuster 112, the position switching unit 124, the detector 125, the pipette controller 136, and the stirring part 140. As will be described later, when the liquid feeding unit 130 provides the liquid containing the specimen to the housing part 211 of the reaction vessel 200 held by the holding part 300, the controller 150 instructs the pipette controller 136 to control the amount of the liquid to be provided in the housing part 211 so that the liquid does not come into contact with the capturing region 226 when the liquid in the housing part 211 is left still and the liquid comes into contact with the capturing region 226 when the liquid in the housing part 211 is stirred. The controller 150 includes, for example, a known computer or microcomputer including an arithmetic device, a control device, a storage device, an input device, and an output device.

Note that, in the present embodiment, the liquid feeding unit 130 and the stirring part 140 are arranged so that introduction and removal of the liquid by the liquid feeding unit 130 and application of vibration by the stirring part 140 can be performed on the reaction vessel 200 arranged at a position where the excitation light α can be emitted, but the positions of the liquid feeding unit 130 and the stirring part 140 are not limited thereto. For example, when the reaction vessel 200 is disposed at the first position, introduction and removal of the liquid by the liquid feeding unit 130 and application of vibration by the stirring part 140 are performed, and when the reaction vessel 200 is disposed at the second position, irradiation of the excitation light α by the excitation light irradiation unit 110 and detection of the fluorescence β by the fluorescence detection unit 120 may be performed. In this case, the detection device 100 further includes a transport unit for moving the reaction vessel 200 to the first position and the second position.

(Detection Method)

Figure 8:
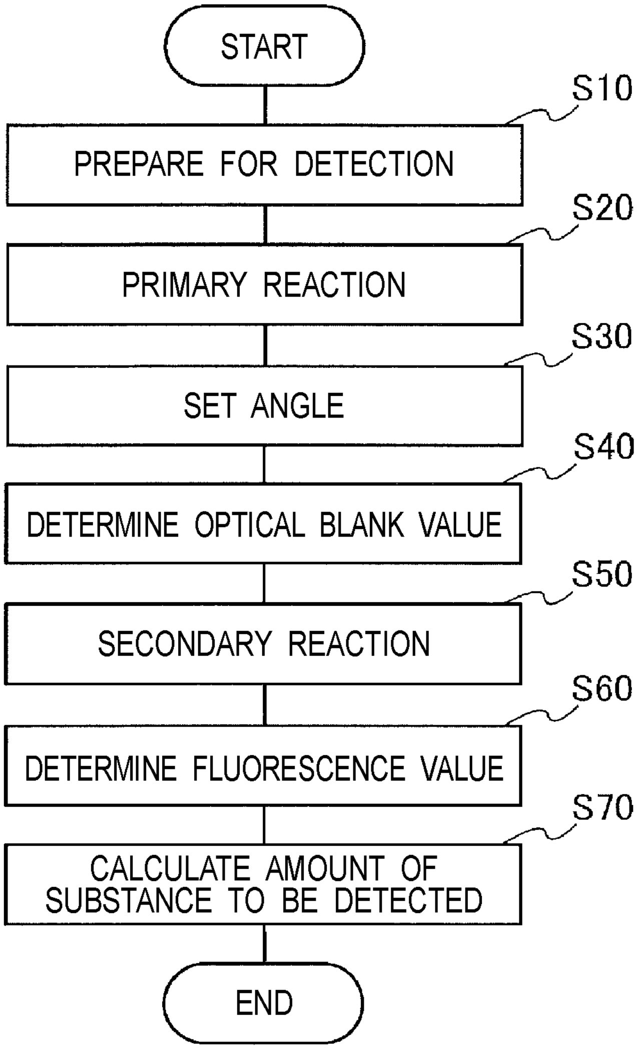
FIG. 8 is a flowchart of a detection method according to an embodiment of the present invention, and is a flowchart illustrating an example of an operation procedure of the detection device.

Next, a detection method of a substance to be detected using the detection device 100 will be described. FIG. 8 is a flowchart illustrating an example of an operation procedure of the detection device 100 when the detection method of the present embodiment is performed.

First, preparation for detection is made (step S10). Specifically, the reaction vessel 200 is installed in the holding part 300. In addition, in a case where a protective agent is present on the capturing region 226 of the reaction vessel 200, the inside of the housing part 211 is cleaned to remove the protective agent on the capturing region 226.

Figure 9A:
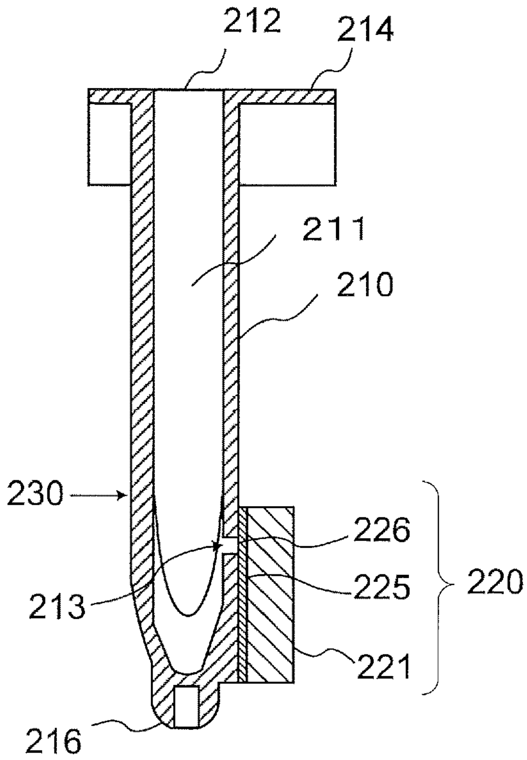
FIG. 9A is a schematic view showing a relationship between a capturing region and a liquid level when a reaction vessel is stirred.

Next, a liquid containing a specimen is provided in the housing part 211 of the reaction vessel 200, and the substance to be detected contained in the liquid is specifically bound to the first capturing body of the capturing region 226 (primary reaction (step S20)). Specifically, the controller 150 controls the pipette controller 136 to provide a liquid containing a specimen in the housing part 211. In addition, the controller 150 controls the stirring part 140 to turn the reaction vessel 200 held by the holding part 300 to stir the liquid in the housing part 211. As a result, the capturing region 226 and the liquid come into contact with each other, and the substance to be detected contained in the liquid binds to the first capturing body of the capturing region 226 (FIG. 9A). At this time, from the viewpoint of appropriately managing the reaction time, it is preferable that the capturing region 226 is positioned above the liquid level 230 of the liquid in the housing part 211 in a state where the liquid in the housing part 211 is not stirred (a state where the liquid is left still) (see FIG. 9B). On the other hand, from the viewpoint of appropriately managing the reaction conditions and the reaction time, in a state where the liquid in the housing part 211 is stirred, the capturing region 226 is preferably always positioned below the liquid level 230 of the liquid being stirred in the housing part 211 (see FIG. 9B). From the viewpoint of efficiently bringing the liquid in the housing part 211 into contact with the capturing region 226, the amount of liquid provided in the housing part 211 is preferably an amount that comes to a position 1 to 3 mm below the height at which the capturing region 226 is disposed. In this way, the reaction time can also be controlled by controlling the stirring time. Therefore, the controller 150 instructs the pipette controller 136 to control the amount of liquid to be provided in the housing part 211 so that the liquid does not come into contact with the capturing region 226 when the liquid in the housing part 211 is left still and the liquid comes into contact with the capturing region 226 when the liquid in the housing part 211 is stirred. Thereafter, the controller 150 controls the pipette controller 136 to remove the specimen in the housing part 211 and to provide a cleaning liquid in the housing part 211 to clean the inside of the housing part 211. Also at this time, the controller 150 controls the stirring part 140 to turn the reaction vessel 200 to stir the cleaning liquid in the housing part 211. At this time, the amount of the cleaning liquid at which the liquid level is higher than the height at which the capturing region 226 is disposed in a stationary state is preferable, but may be lower. Thereafter, the controller 150 controls the pipette controller 136 to remove the cleaning liquid in the housing part 211 and introduce the measurement buffer solution into the housing part 211. The measurement buffer solution is introduced so that the liquid level of the measurement buffer solution is positioned above the capturing region 226 even in a stationary state.

The type of the specimen and the substance to be detected is not particularly limited. Examples of the specimen include body fluids such as blood, serum, plasma, cerebrospinal fluid, urine, nasal fluid, saliva, and semen, tissue extracts, and diluents thereof. Examples of the substance to be detected contained in these specimens include nucleic acids (DNA, RNA, etc.), proteins (polypeptides, oligopeptides, etc.), amino acids, carbohydrates, lipids, and modified molecules thereof.

Next, the incident angle of the excitation light α with respect to the reflecting surface 223 (metal film 225) of the reaction vessel 200 is set to the enhancement angle (step S30). Specifically, the controller 150 controls the light source unit 111 and the first angle adjuster 112 to scan the incident angle of the excitation light α with respect to the reflecting surface 223 while irradiating the position corresponding to the capturing region 226 of the reflecting surface 223 with the excitation light α. At the same time, the controller 150 controls the detector 125 to detect the plasmon scattered light γ. At this time, the controller 150 controls the position switching unit 124 to move the optical filter 122 out of the optical path. The controller 150 obtains data including the relationship between the incident angle of the excitation light α and the intensity of the plasmon scattered light γ. Then, the controller 150 analyzes the data and determines the incident angle (enhancement angle) at which the intensity of the plasmon scattered light γ is maximized. Finally, the controller 150 controls the first angle adjuster 112 to set the incident angle of the excitation light α with respect to the reflecting surface 223 to the enhancement angle.

The enhancement angle is determined by the material and shape of the prism 221, the thickness of the metal film 225, the refractive index of the liquid in the housing part 211, and the like, but slightly varies due to various factors such as the type and amount of the liquid in the housing part 211 and the shape error of the prism 221. Therefore, it is preferable to determine the enhancement angle each time detection is performed. The enhancement angle is determined on the order of about 0.1°.

Next, an optical blank value is measured (step S40). Specifically, the controller 150 controls the light source unit 111 to irradiate the position corresponding to the capturing region 226 of the reflecting surface 223 with the excitation light α. At the same time, the controller 150 controls the detector 125 to detect the light amount of the background light having the same wavelength as the fluorescence β. At this time, the controller 150 controls the position switching unit 124 to move the optical filter 122 onto the optical path. The controller 150 records the measured light amount of the background light as a blank value.

Next, the second capturing body labeled with the fluorescent substance is bound to the substance to be detected bound to the first capturing body on the metal film 225 (secondary reaction (step S50)). Here, the second capturing body is a substance that specifically binds to a site of the substance to be detected different from a site to which the first capturing body specifically binds. In addition, a fluorescent substance is bound to the second capturing body. Therefore, when the labeling liquid is provided in the housing part 211, the second capturing body specifically binds to the substance to be detected bound to the first capturing body, and the substance to be detected is indirectly labeled with the fluorescent substance. The second capturing body only needs to be a substance that specifically binds to a site different from a site where the first capturing body specifically binds to the substance to be detected, and may be a biological molecule specific to the substance to be detected, a fragment thereof, or the like. In addition, the second capturing body may be composed of one molecule, or may be a complex in which two or more molecules are bound.

Figure 9B:
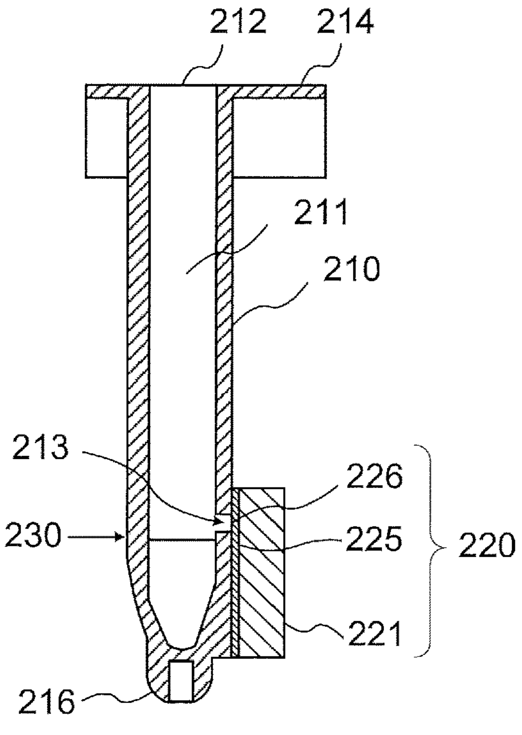
FIG. 9B is a schematic view showing a relationship between a capturing region and a liquid level when the reaction vessel is left still.

Specifically, the controller 150 controls the pipette controller 136 to remove the measurement buffer solution in the housing part 211 and introduce the labeling liquid containing the second capturing body into the housing part 211. In addition, the controller 150 controls the stirring part 140 to turn the reaction vessel 200 to stir the labeling liquid in the housing part 211. Also at this time, from the viewpoint of appropriately managing the reaction time, as shown in FIG. 9B, in a state where the liquid (labeling liquid) in the housing part 211 is not stirred (in a state of being left still), the capturing region 226 is preferably positioned above the liquid level 230 of the liquid in the housing part 211. On the other hand, from the viewpoint of appropriately managing the reaction conditions and the reaction time, in a state where the liquid in the housing part 211 is stirred, the capturing region 226 is preferably always positioned below the liquid level 230 of the liquid being stirred in the housing part 211 (see FIG. 9A). From the viewpoint of efficiently bringing the liquid in the housing part 211 into contact with the capturing region 226, the amount of liquid provided in the housing part 211 is preferably an amount that comes to a position 1 to 3 mm below the height at which the capturing region 226 is disposed. In this way, the reaction time can also be controlled by controlling the stirring time. Therefore, the controller 150 instructs the pipette controller 136 to control the amount of liquid to be provided in the housing part 211 so that the liquid does not come into contact with the capturing region 226 when the liquid in the housing part 211 is left still and the liquid comes into contact with the capturing region 226 when the liquid in the housing part 211 is stirred. Thereafter, the controller 150 controls the pipette controller 136 to remove the labeling liquid in the housing part 211 and to provide the cleaning liquid in the housing part 211 to clean the inside of the housing part 211. Also at this time, the controller 150 controls the stirring part 140 to turn the reaction vessel 200 to stir the cleaning liquid in the housing part 211. At this time, the amount of the cleaning liquid at which the liquid level is higher than the height at which the capturing region 226 is disposed in a stationary state is preferable, but may be lower. Furthermore, the controller 150 controls the pipette controller 136 to remove the cleaning liquid in the housing part 211 and to provide the measurement buffer solution in the housing part 211. The measurement buffer solution is introduced so that the liquid level of the measurement buffer solution is positioned above the capturing region 226 even in a stationary state.

Next, the fluorescence value from the fluorescent substance that labels the substance to be detected is measured (step S60). Specifically, the controller 150 controls the light source unit 111 to irradiate the position corresponding to the capturing region 226 of the reflecting surface 223 with the excitation light α. At the same time, the controller 150 controls the detector 125 to detect the amount of light having the same wavelength as the fluorescence β. At this time, the controller 150 controls the position switching unit 124 to move the optical filter 122 onto the optical path. The controller 150 records the measured light amount as a fluorescence value.

Finally, the presence or amount of the substance to be detected is calculated (step S70). The fluorescence value mainly includes a fluorescence component (signal value) derived from a fluorescent substance that labels the substance to be detected and an optical blank value. Therefore, the controller 150 can calculate a signal value correlated with the amount of the substance to be detected by subtracting the optical blank value obtained in step S40 from the fluorescence value obtained in step S60. Then, the signal value is converted into the amount, concentration, and the like of the substance to be detected by a calibration curve prepared in advance.

According to the above procedure, the presence or amount of the substance to be detected contained in the specimen can be detected with high accuracy and reproducibility.

Note that, in the above description, the incident angle of the excitation light α is set to the enhancement angle in step S30, but the incident angle of the excitation light α may be set to the resonance angle in step S30. In this case, the incident angle of the excitation light α with respect to the reflecting surface 223 is scanned, and the light amount of the reflected light α' of the excitation light is detected by a separately installed reflected light detector. Then, the incident angle of the excitation light α when the light amount of the reflected light α' becomes minimum is determined as the resonance angle.

(Effects)

As described above, according to the detection device 100 and the detection method of the present embodiment, the amount of the liquid containing the specimen to be provided in the housing part 211 of the reaction vessel 200 and the position of the capturing region 226 of the reaction vessel 200 are controlled so that the liquid and the capturing region 226 are brought into contact with each other only at the time of stirring, whereby the substance to be detected can be detected with high accuracy and high accuracy and high reproducibility even when the amount of the specimen is small.

Note that, in the present embodiment, the detection device and the detection method using the SPFS have been described, but the detection device and the detection method according to the present embodiment are not limited thereto. For example, the detection device and the detection method according to the present embodiment may detect the substance to be detected using the SPR method. In this case, the detector 125 detects not the fluorescence β but the excitation light α' reflected by the reflecting surface 223 of the prism 221 as the light emitted from the reaction vessel 200 and the light whose light amount changes depending on the amount of the substance to be detected captured in the capturing region 226.

[Modification]

In the above-described embodiment, the detection device and the detection method using the holding part 300 in which the first substrate 310, the second substrate 311, and the third substrate 312 are separate bodies have been described, but the detection device and the detection method of the present disclosure are not limited thereto. For example, a holding part 500 as illustrated in FIG. 10A may be used.

Figure 10A:
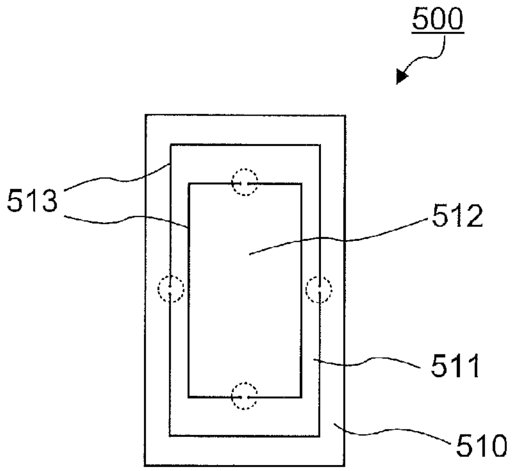
FIG. 10A is a plan view illustrating a modification of the holding part for holding the holding part of the container according to an embodiment of the present disclosure.

As illustrated in FIG. 10A, the holding part 500 is manufactured by forming a plurality of cuts 513 in one plate. The plurality of cuts 513 are formed between the first substrate 510 and the second substrate 511 and between the second substrate 511 and the third substrate 512 while leaving a portion surrounded by a dotted circle so that the holding part 500 can perform the same movement as the holding part 300 during stirring of the reaction vessel 200. A portion surrounded by a dotted circle functions as a first rotation shaft and a second rotary shaft.

Figure 10B:
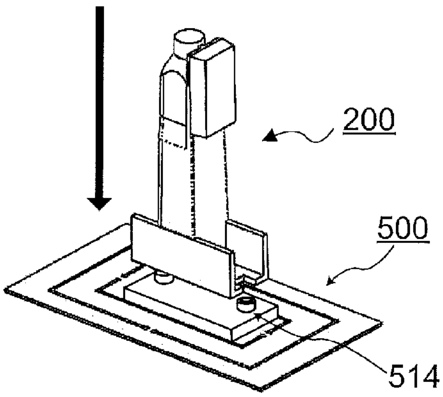
FIG. 10B is a perspective view illustrating a position where the container is attached to the holding part.
Figure 10C:
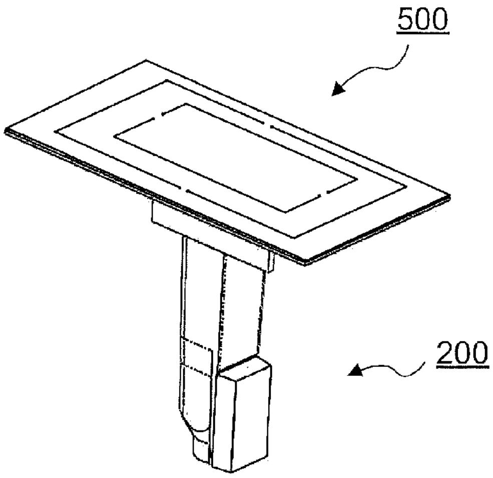
FIG. 10C is a perspective view of the reaction vessel in a state where the holding part is attached.

As shown in FIG. 10B, the reaction vessel 200 is attached to the back surface side of the holding part 500 in the direction of the arrow, and is used in the state shown in FIG. 10C. As a result, when the stirring part 140 turns the bottom portion 216 of the container 210, each substrate of the holding part 500 moves in accordance with the movement of the container 210, so that the liquid in the housing part 211 is stirred in a swirling manner and can come into contact with the capturing region 226.

Note that, the material and thickness of the plate material constituting the holding part 500 are not particularly limited as long as the plate material has strength enough to withstand stirring. Further, the reaction vessel 200 and the holding part 500 are fixed by attaching the recess 215 of the reaction vessel 200 to a protrusion 514 formed in the holding part 500, but a method for fixing the reaction vessel 200 and the holding part 500 is not particularly limited.

Figure 11:
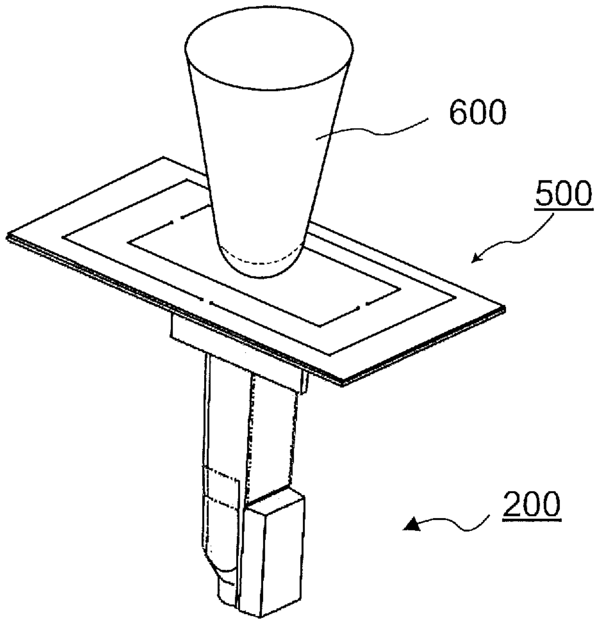
FIG. 11 is a perspective view illustrating a state in which a turning shaft is disposed on an upper surface of the holding part.

As shown in FIG. 11, a turning shaft 600 may be used to turn the reaction vessel 200 attached to the holding part 500. By placing and sliding the turning shaft 600 on the holding part 500, the reaction vessel 200 can be turned to efficiently stir the liquid in the housing part 211. Note that, in FIG. 11, the tip of the turning shaft 600 has a substantially circular shape, but the tip shape of the turning shaft 600 is not particularly limited as long as it can be in point contact with the upper surface of the holding part 500.

The present application claims priority based on Japanese Patent Application No. 2019-173299 filed on Sep. 24, 2019. The contents described in the specification and drawings of this application are all incorporated herein by reference.

INDUSTRIAL APPLICABILITY

The detection device and the detection method according to the present disclosure are useful for, for example, clinical tests and the like.

The invention claimed is:

1. A detection device for detecting a substance to be detected in a specimen, the detection device comprising:

- a reaction vessel including:
  - a container including a housing part for holding a specimen, the container having a first opening opened at a top of the container and a second opening opened at a side of the container; and
  - a side wall member disposed on the side of the container, the side wall member including a prism, a metal film disposed on the prism, and a capturing region for capturing a substance to be detected disposed on the metal film, the side wall member being fixed to the container so that the capturing region is exposed in the second opening, a controller configured to control operations of the detection device;
- a holding part for holding the reaction vessel;
- a specimen providing unit that provides a liquid containing the specimen through the first opening to the housing part of the reaction vessel held by the holding part;
- a light source positioned outside of the container to irradiate light toward the metal film of the reaction vessel held by the holding part so that surface plasmon resonance occurs in the metal film;
- a detector positioned outside of the container and configured to detect light emitted from the reaction vessel when the light source irradiates the metal film with light, the detector configured to detect light having an amount corresponding to an amount of the substance to be detected captured in the capturing region; and
- a stirring part for stirring the liquid in the housing part of the reaction vessel, wherein
- the reaction vessel further includes;
  - an upper support portion connected to a region adjacent to the top of the container and supported by the holding part; and a stirring-contact portion configured to contact the stirring part, the holding part includes:

a first rotary shaft extending in a first direction and configured to rotatably support the upper support portion in a first rotation direction; and a second rotary shaft extending in a second direction orthogonal to the first direction and configured to rotatably support the upper support portion in a second rotation direction, the stirring part is in contact with the stirring-contact portion, and the stirring part stirs the liquid in the housing part by turning the stirring-contact portion in a state where the upper support portion is rotatably supported by the holding part.

2. The detection device according to claim 1, wherein the container includes a protrusion having a spherical segment shape, the stirring part includes a conical recess, and the protrusion and the conical recess are configured to be engaged with each other.

3. The detection device according to claim 1, wherein the container includes a conical recess, the string portion includes a protrusion having a spherical segment shape, and the conical recess and the protrusion are configured to be engaged with each other.

4. The detection device according to claim 1, wherein the detector detects fluorescence emitted from a fluorescent substance that labels the substance to be detected captured in the capturing region when the light source irradiates the metal film with light.

* * * * *